United States Patent

Neustadt et al.

Patent Number: 5,356,925
Date of Patent: Oct. 18, 1994

[54] N-(MERCAPTOALKYL)UREAS AND CARBAMATES

[75] Inventors: Bernard R. Neustadt, West Orange; Alan Bronnenkant, Verona, both of N.J.

[73] Assignee: Schering Corporation, Kenilworth, N.J.

[21] Appl. No.: 969,163

[22] PCT Filed: Aug. 14, 1991

[86] PCT No.: PCT/US91/05587

§ 371 Date: Feb. 11, 1993

§ 102(e) Date: Feb. 11, 1993

[87] PCT Pub. No.: WO92/03410

PCT Pub. Date: Mar. 5, 1992

Related U.S. Application Data

[63] Continuation-in-part of Ser. No. 568,569, Aug. 16, 1990, Pat. No. 5,173,506.

[51] Int. Cl.$^5$ .............. A61K 31/165; A61K 31/385; C07C 327/08

[52] U.S. Cl. ................... 514/435; 514/513; 514/618; 558/251; 558/252; 558/254; 560/16; 564/162; 564/163; 564/192; 564/193

[58] Field of Search .............. 560/16; 514/435, 513, 514/212, 330, 423, 487, 538, 618; 558/254, 252, 251; 540/608; 546/245; 548/540; 564/56, 192, 193, 162, 163; 206/569

[56] References Cited

U.S. PATENT DOCUMENTS

| | | | |
|---|---|---|---|
| 4,105,776 | 8/1978 | Ondetti et al. | 424/274 |
| 4,256,761 | 3/1981 | Suh et al. | 424/282 |
| 4,344,949 | 8/1982 | Hoefle et al. | 424/258 |
| 4,350,704 | 9/1982 | Hoefle et al. | 424/274 |

(List continued on next page.)

FOREIGN PATENT DOCUMENTS 46953  3/1982  European Pat. Off. .

(List continued on next page.)

OTHER PUBLICATIONS

Needleman et al., *N. Engl. J. Med.*, 314, 13, (1986), pp. 828–834.

(List continued on next page.)

*Primary Examiner*—Johann Richter
*Assistant Examiner*—Joseph K. McKane
*Attorney, Agent, or Firm*—Anita W. Magatti; Eric S. Dicker

[57] ABSTRACT

Novel N-(mercaptoalkyl)urea or carbamates of the formulae I and II

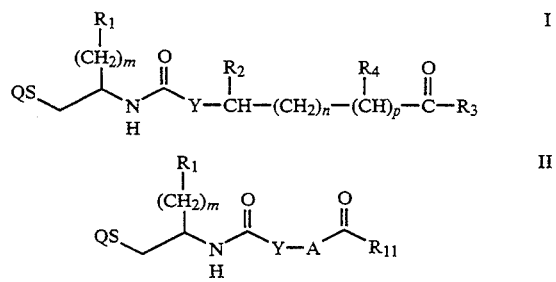

wherein

A is a monocyclic or bicyclic arylene or heteroarylene;

Q is hydrogen or $R_9CO$—;

Y is —O—, —S— or —$NR_8$—;

$R_1$ is lower alkyl, cyclolower alkyl, aryl or heteroaryl;

$R_2$ and $R_8$ are independently hydrogen; lower alkyl; cyclolower alkyl; substituted lower alkyl; aryl; or heteroaryl;

$R^3$ is —$OR_5$ or —$NR_5R_6$;

$R_4$ is —$(CH_2)_qR_7$; or $R_2$ and $R_4$ and the carbons to which they are attached complete a ring;

$R_5$ and $R_6$ are hydrogen, lower alkyl, hydroxy lower alkyl, lower alkoxy lower alkyl or aryl lower alkyl, or $R_5$ and $R_6$ together with the nitrogen to which they are attached form a ring;

and the pharmaceutically acceptable salts thereof useful in the treatment of cardiovascular disorders, nephrotoxicity and pain conditions and combinations of N-(mercaptoalkyl)ureas or carbamates and atrial natriuretic factors or angiotensin convening enzyme inhibitors useful for treating cardiovascular disorders are disclosed.

10 Claims, No Drawings

U.S. PATENT DOCUMENTS

| | | | |
|---|---|---|---|
| 4,374,829 | 2/1983 | Harris et al. | 424/177 |
| 4,374,847 | 2/1983 | Gruenfeld | 424/274 |
| 4,410,520 | 10/1983 | Watthey | 424/244 |
| 4,462,943 | 7/1984 | Petrillo et al. | 260/112 |
| 4,468,519 | 8/1984 | Krapcho | 548/409 |
| 4,470,972 | 9/1984 | Gold et al. | 424/177 |
| 4,470,973 | 9/1984 | Natarajan et al. | 424/177 |
| 4,508,729 | 4/1985 | Vincent et al. | 514/435 |
| 4,512,924 | 4/1985 | Attwood et al. | 260/243.3 |
| 4,513,009 | 4/1985 | Roques et al. | 514/435 |
| 4,555,506 | 11/1985 | Karanewsky et al. | 514/435 |
| 4,740,499 | 4/1988 | Olins | 514/435 |
| 4,749,688 | 7/1988 | Sybertz | 514/435 |
| 4,774,256 | 9/1988 | Delaney et al. | 514/435 |
| 4,801,609 | 1/1989 | Haslanger et al. | 514/435 |

FOREIGN PATENT DOCUMENTS

| | | |
|---|---|---|
| 50800 | 5/1982 | European Pat. Off. . |
| 79022 | 5/1983 | European Pat. Off. . |
| 79522 | 5/1983 | European Pat. Off. . |
| 161769 | 11/1985 | European Pat. Off. . |
| 8905796 | 6/1989 | PCT Int'l Appl. ............ 514/435 |
| 9002117 | 3/1990 | PCT Int'l Appl. . |
| 9003364 | 4/1990 | PCT Int'l Appl. ............ 514/435 |
| 9012003 | 10/1990 | PCT Int'l Appl. . |
| 8400670 | 9/1985 | South Africa . |
| 2095682 | 10/1982 | United Kingdom . |
| 2207351 | 1/1989 | United Kingdom . |

OTHER PUBLICATIONS

Cantin et al., *Sci. Amer.*, 254, (1986), pp. 76–81.

Wyvratt et al., *Med. Res. Rev.*, 5, 4, (1985), pp. 483–531.

Capasso et al., *Am. J. Hyper.*, 3, 3, (1990), pp. 204–210.

Burger, ed., *Medicinal Chemistry*, 2nd ed., (1960), (Interscience Publ., In New York), pp. 565–601.

Senkelwalter, et al., *Hypotensive Drugs; Progress in Drug Research*, vol. 10, (1960), (Birkhauser Verlag, Basel), pp. 510–512.

Bolis, et al., *J. Med. Chem.*, 30, (1987), pp. 1724–1737.

Plattner, et al., *J. Med. Chem.*, 31, (1988), pp. 2277–2288.

Haber, et al., *J. Cardiovas. Pharmacol.*, 10, (1987), pp. 554–558.

CA 116(23):235102n, Preparation of . . . carbonylation. Funaioli et al., p. 772, 1992.

CA 117(1):7673q, N–(Mercaptoalkyl)ureas . . . preparation. Neustadt et al., p. 775, 1992.

N-(MERCAPTOALKYL)UREAS AND CARBAMATES

The present application is to a continuation-in-part of U.S. application Ser. No. 07/568,569, U.S. Pat. No. 5,123,506, filed Aug. 16, 1990, U.S. Pat. No. 5,173,506, the benefit of which applications are claimed pursuant to the provisions of 35 U.S.C. §§120, 363 and 365(C).

BACKGROUND OF THE INVENTION

The present invention relates to novel N-(mercaptoalkyl)ureas and carbamates useful in the treatment of cardiovascular disorders and pain conditions.

Cardiovascular disorders which may be treated with compounds of the present invention include hypertension, congestive heart failure, edema and renal insufficiency.

Human hypertension represents a disease of multiple etiologies. Included among these is a sodium and volume dependent low renin form of hypertension. Drugs that act to control one aspect of hypertension will not necessarily be effective in controlling another.

Enkephalin is a natural opiate receptor agonist which is known to produce a profound analgesia when injected into the brain ventricle of rats. It is also known in the art that enkephalin is acted upon by a group of enzymes known generically as enkephalinases, which are also naturally occurring, and is inactivated thereby.

A variety of mercaptoacylamino acids are known as enkephalinase inhibitors useful as analgesics and in the treatment of hypertension. U.S. Pat. No. 4,774,256 discloses compounds of the formula

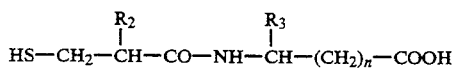

wherein n is 1-15 and $R_2$ and $R_3$ are various aryl, arylalkyl and heteroarylalkyl groups. The compounds are disclosed as having enkephalinase inhibiting activity.

U.S. Pat. No. 4,801,609 to Haslanger et al. disclosed antihypertensive compounds of the formula

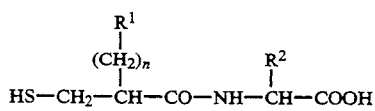

wherein n is 0 or 1; $R^1$ is substituted phenyl and $R^2$ is substituted alkyl, phenyl or heteroaryl.

U.S. Pat. No. 4,513,009 to Roques et al. disclosed similar compounds and those having the formula

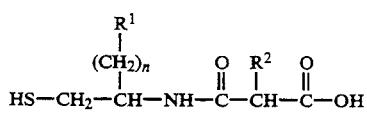

wherein $R^1$ includes alkyl and optionally substituted phenyl, n is 0 or 1 and $R^2$ includes phenyl and substituted alkyl. The compounds are disclosed by Roques et al as principally having enkephalinase inhibitory activity, but are also said to be antihypertensives.

European Patent Application 161,769 discloses enkephalinase inhibitors of the formula

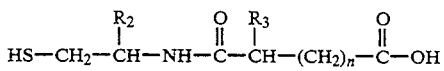

wherein $R_2$ includes alkyl, aryl and arylalkyl, $R_3$ includes alkyl, aryl, heteroaryl, arylalkyl and heteroarylalkyl, and n is 1-15.

It is known that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homeostasis", *N. Engl. J. Med.*, 314, 13 (1986) pp. 828–834, and M. Cantin et al in "The Heart as an Endocrine Gland", *Scientific American*, 254 (1986) pg. 7681. U.S. Pat. No. 4,740,499 to Olins discloses a method of prolonging the effect of atrial peptides comprising co-administering thiorphan (a compound within the scope of U.S. Pat. No. 4,513,009) or kelatorphan with an atrial peptide.

A class of drugs known to be effective in treating some types of hypertension is ACE inhibitors, which compounds are useful in blocking the rise in blood pressure caused by increases in vascular resistance and fluid volume due to the formation of angiotensin II from angiotensin I. For a review of ACE inhibitors, see M. Wyvratt and A. Patchett, "Recent Developments in the Design of Angiotensin Converting Enzyme Inhibitors" in *Med. Res. Rev.* Vol. 5, No. 4 (1985) pp. 483–531.

SUMMARY OF THE INVENTION

Novel compounds of the present invention are represented by the formulae

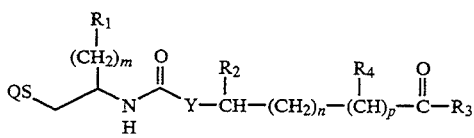

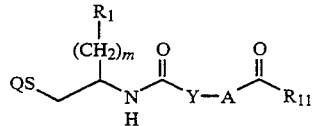

wherein
A is a monocyclic or bicyclic arylene or heteroarylene;
Q is hydrogen or $R_9CO—$;
Y is $—O—$, $—S—$ or $—NR_8—$;
$R_1$ is lower alkyl, cyclolower alkyl, aryl or heteroaryl;
$R_2$ and $R_8$ are independently hydrogen; lower alkyl; cyclolower alkyl; lower alkyl substituted with hydroxy, lower alkoxy, mercapto, lower alkylthio, aryl or heteroaryl; aryl; or heteroaryl;
$R_3$ is $—OR_5$ or $—NR_5R_6$;
$R_4$ is $—(CH_2)_qR_7$; or $R_2$ and $R_4$ together with the carbons to which they are attached complete a 5-, 6- or 7-membered carbocyclic ring;
$R_5$ and $R_6$ are independently selected from the group consisting of hydrogen, lower alkyl, hydroxy lower alkyl, lower alkoxy-lower alkyl and aryl lower alkyl, or $R_5$ and $R_6$ together with the nitrogen to which they are attached form a 5-, 6- or 7-membered ring wherein said $R_5$ and $R_6$ together comprise a C4 to C6 alkylene chain;

$R_7$ is hydrogen, hydroxy, lower alkoxy, lower alkanoyloxy, mercapto, lower alkylthio, aryl or heteroaryl;

$R_9$ is hydrogen, lower alkyl or aryl;

m is 1 or 2;

n is 0, 1 or 2;

p is 0 or 1; and q is 0, 1 or 2;

and the pharmaceutically acceptable salts thereof.

A preferred group of compounds of formula I of the present invention is that wherein p is zero. Also preferred compounds of formula I are those wherein p is zero and n is zero or 1. A third preferred group of compounds is that wherein Y is —O— or —$NR_8$—. Still another preferred group of compounds of formula I is that wherein $R_2$ is hydrogen. For compounds of formula I wherein Y is —$NR_8$—, $R_8$ is preferably hydrogen or phenyl.

A preferred group of compounds of formula II is that wherein A is phenylene. Also preferred are compounds of formula II wherein Y is —O— or —NH—.

For compounds of formulae I and II, preferred values for Q are hydrogen and acyl. Other preferred compounds of formula I and II are those wherein $R_1$ is phenyl or lower alkyl-substituted phenyl, for example tolyl. Yet another preferred group of compounds is that wherein $R_3$ is hydroxy, lower alkoxy or aryl lower alkoxy. A preferred value for m is 1.

Especially preferred compounds of formula I are those wherein Y is —O— or —$NR_8$— wherein $R_8$ is hydrogen or phenyl; $R_1$ is phenyl or tolyl; m is 1; $R_2$ is hydrogen; p is 0; and $R_3$ is hydroxy or lower alkoxy.

Especially preferred compounds of formula II are those wherein Y is —O— or —NH—, $R_1$ is phenyl or tolyl, m is 1, A is phenylene and $R_3$ is hydroxy or alkoxy.

The invention also relates to the treatment of cardiovascular diseases with a combination of an N-(mercaptoalkyl)urea or carbamate of the present invention and an atrial natriuretic factor (ANF) and with a combination of an N-(mercaptoalkyl)urea or carbamate of the present invention and an angiotensin converting enzyme (ACE) inhibitor.

Other aspects of the invention relate to pharmaceutical compositions comprising an N-(mercaptoalkyl)urea or carbamate of this invention, alone or in combination with an ANF or an ACE inhibitor, and to methods of treatment of cardiovascular diseases comprising administering an N-(mercaptoalkyl)urea or carbamate of this invention, alone or in combination with an ANF or an ACE inhibitor, to a mammal in need of such treatment.

Still another aspect of the invention relates to a method of treating pain conditions by administering an N-(mercaptoalkyl)urea or carbamate of this invention, thereby inhibiting the action of enkephalinase in a mammal and eliciting an analgesic effect. Analgesic pharmaceutical compositions comprising said N-(mercaptoalkyl)ureas or carbamates are also contemplated.

An additional aspect of the invention relates to a method of treating nephrotoxicity resulting from immunosuppression therapy by administration of an N-(mercaptoalkyl)urea or carbamate of this invention.

DETAILED DESCRIPTION

As used herein, the term "lower alkyl" means straight or branched alkyl chains of 1 to 6 carbon atoms, and "lower alkoxy" similarly refers to alkoxy groups having 1 to 6 carbon atoms. Cyclolower alkyl means cyclic alkyl groups of 3 to 6 carbon atoms.

"Aryl" means mono-cyclic or fused ring bicyclic carbocyclic aromatic groups having 6 to 10 ring members and "heteroaryl" means mono-cyclic or fused ring bicyclic aromatic groups having 5-10 ring members wherein 1-2 ring members are independently nitrogen, oxygen or sulfur, wherein the carbon ring members of the aryl and heteroaryl groups are substituted by zero to three substituents selected from the group consisting of lower alkyl, hydroxy, halo, lower alkoxy, cyclolower alkyl, cyano, aminomethyl, trifluoromethyl, phenyl, phenoxy or phenylthio. Examples of carbocyclic aryl groups are phenyl, α-naphthyl and β-naphthyl, and examples of heterocyclic aryl groups are furyl, thienyl, pyrrolyl, benzofuryl, benzothienyl, indolyl and pyridyl. All positional isomers, e.g. 2-pyridyl, 3-pyridyl, are contemplated.

"Alkylene" means a bivalent chain of methylene groups, e.g., a group of the formula —$(CH_2)_x$—, wherein x is 4, 5 or 6.

"Arylene" means a bivalent phenyl group or a fused ring bicyclic carbocyclic aromatic group joined to the molecule by a bivalent phenyl group, e.g. a group of the formula

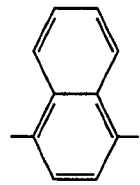

"Heteroarylene" similarly means a bivalent monocyclic or fused ring bicyclic heteroaryl group.

"Halo" refers to fluorine, chlorine, bromine or iodine radicals.

Certain compounds of the invention are acidic e.g., those compounds which possess a carboxyl group. These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

The salts may be formed by conventional means, as by reacting the free acid form of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formulae I and II have at least one asymmetrical carbon atom and therefore include various stereoisomers. The invention includes all such isomers both in pure form and in admixture, including racemic mixtures.

An aspect of the present invention described above relates to the combination of a compound of formulae I or II with an ANF. As indicated by Needleman et al., a number of ANF have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occuring ANF's also have been found to have comparable biological activity. Examples of ANFs contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence of each of the above wherein Met 12 is Ile.

Another aspect of the invention is the administration of a combination of an ACE inhibitor and a compound of formula I or II. Examples of ACE inhibitors are those disclosed in the article by Wyvratt et al., cited above. The following Table II lists ACE inhibitors preferred for use in the combination of this invention.

TABLE II

PREFERRED ACE INHIBITORS $$\underset{R-CH-NH-CH-C-R_3}{\overset{COOR_1 \quad R_2 \quad O}{|\quad\quad |\quad\quad \|}}$$

| | R | $R_1$ | $R_2$ | $R_3$ |
|---|---|---|---|---|
| spirapril | $C_6H_5CH_2CH_2-$ | Et | $CH_3$ | 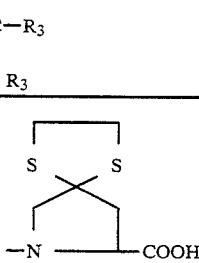 |
| enalapril | $C_6H_5CH_2CH_2-$ | Et | $CH_3$ | prolyl |
| ramipril | $C_6H_5CH_2CH_2-$ | Et | $CH_3$ | 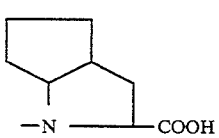 |
| perindopril | $CH_3CH_2CH_2-$ | Et | $CH_3$ | 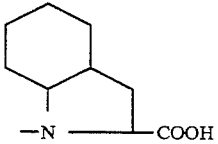 |
| indolapril | $C_6H_5CH_2CH_2-$ | Et | $CH_3$ | 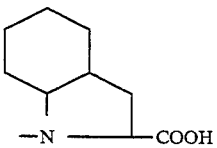 |
| lysinopril | $C_6H_5CH_2CH_2-$ | H | $NH_2(CH_2)_4-$ | prolyl |
| quinapril | $C_6H_5CH_2CH_2-$ | Et | $CH_3$ | 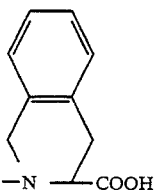 |
| pentopril ($NH=CH_2$) | $CH_3$ | Et | $CH_3$ | 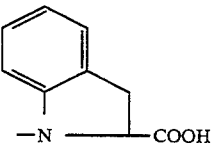 |

TABLE II-continued
PREFERRED ACE INHIBITORS

| | | | |
|---|---|---|---|
| cilazapril | $C_6H_5CH_2CH_2-$ | H | $-\overset{R_2}{\underset{|}{CH}}-\overset{O}{\underset{||}{C}}-R_3$ is [bicyclic structure with N, N, O, COOH] |

$$RS-CH_2-\overset{CH_3}{\underset{|}{CH}}-\overset{O}{\underset{||}{C}}-R_2$$

| | R | R₂ |
|---|---|---|
| captopril | H | prolyl |
| zofenopril | $C_6H_5CO-$ | [pyrrolidine with $SC_6H_5$ substituent, $-N$, COOH] |
| pivalopril | $(CH_3)_3C-\overset{O}{\underset{||}{C}}-$ | [cyclopentyl-$N-CH_2.COOH$] |

$$R-\overset{O}{\underset{||}{\underset{|}{P}}}-CH_2-\overset{O}{\underset{||}{C}}-N\overset{R^2}{\diagup}-COOH$$
$$OR^1$$

| | R | R¹ | R² |
|---|---|---|---|
| fosinopril | $C_6H_5-(CH_2)_4-$ | $\begin{array}{c}(CH_3)_2\\|\\CH\\|\\-CH-O-\overset{O}{\underset{||}{C}}-CH_2CH_3\end{array}$ | $C_6H_5-$ |

Compounds of the present invention can be made by methods well known to those skilled in the art. Two examples of synthetic methods are shown in Routes 1 and 2. In both routes, acid III is converted into isocyanate IV, for example by reaction with diphenylphosphorylazide at elevated temperatures (e.g. 80° C.) in the presence of a base such as triethylamine in a solvent such as toluene. The isocyanate need not be isolated. In Route 1, IV is reacted with an amine, alcohol, or thiol of formula V or VI to obtain compounds of formula I or II, respectively:

ROUTE 1:

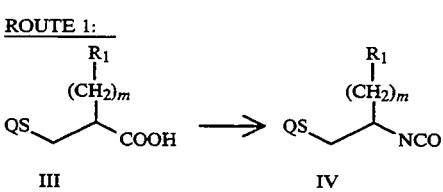

ROUTE 1: -continued

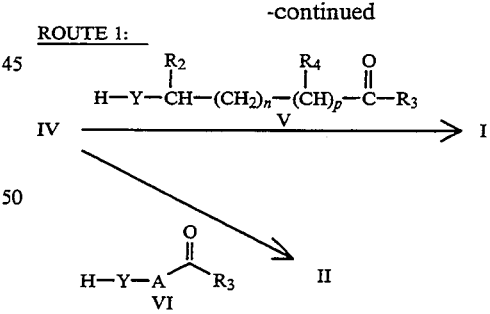

wherein Q, Y, A, R₁, R₂, R₃, R₄, m, n, and p are as defined above.

In Route 2, the isocyanate IV is treated with benzyl alcohol to produce the benzyl carbamate, VII. The carbamate VII is then convened to an amine VIII or a reactive derivative thereof, typically an amine salt, for example by treatment with an acid, preferably HBr. The amine or reactive derivative is then reacted with a compound of formula IX or X in an inert solvent such as methylene chloride in the presence of a base such as triethylamine at room temperature to obtain compounds of formula I or II, respectively:

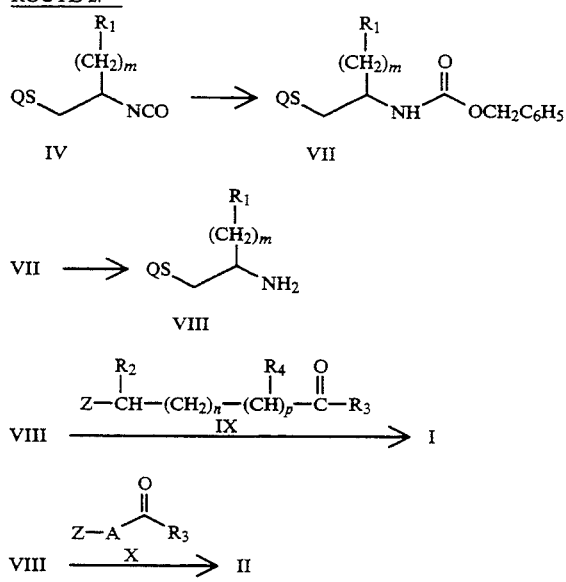

ROUTE 2:

wherein Q, A, $R_1$, $R_2$, $R_3$, $R_4$, m, n, and p are as defined above, and wherein Z is —NCO, —N($R_8$)COCl, or —OC(O)Cl, to obtain compounds wherein Y is —NH—, —$NR_8$—, and —O—, respectively.

In both routes, the use of suitable protecting groups may be employed. The groups Q and $R^3$ can act as protecting groups.

It is apparent that using methods well known to those skilled in the art, compounds of formula I and II can be converted to different compounds of formula I and II, respectively, by appropriate reaction of the Q and/or $R^3$ variables, e.g. a thioester can be converted to a mercaptan and an acid can be converted to an amide or an ester to an acid.

Compounds of formula III, V, VI, IX and X are known in the art or can be prepared by methods well known in the art.

We have found that the novel compounds of the present invention are effective in treating cardiovascular disorders such as congestive heart failure, edema, renal insufficiency and various types of hypertension, particularly volume expanded hypertension. These novel compounds enhance both the magnitude and duration of the antihypertensive and natriuretic effects of endogenous ANF. Administration of a combination of an N-(mercaptoalkyl)urea or carbamate and an ACE inhibitor provides an antihypertensive and anticongestive heart failure effect greater than either the N-(mercaptoalkyl)urea or carbamate or ACE inhibitor alone. Administration of a combination of an N-(mercaptoalkyl)urea or carbamate of formula I or II and an exogenous ANF or ACE inhibitor is therefore particularly useful in treating hypertension or congestive heart failure.

In addition to the compound aspect, the present invention therefore also relates to treating cardiovascular disorders with an N-(mercaptoalkyl)urea or carbamate of formula I or II or with an N-(mercaptoalkyl)urea or carbamate of formula I or II in combination with an ANF or an ACE inhibitor, which methods comprise administering to a mammal in need of such treatment an amount of the N-(mercaptoalkyl)urea or carbamate effective to treat hypertension or congestive heart failure or an amount of a combination of an N-(mercap- toalkyl)urea or carbamate and ANF or ACE inhibitor effective to treat hypertension or congestive heart failure. The drug or combination of drugs is preferably administered in a pharmaceutically acceptable carder, e.g. for oral or parenteral administration. The combinations of drugs may be co-administered in a single composition, or components of the combination therapy may be administered separately. Where the components are administered separately, any convenient combination of dosage forms may be used, e.g. oral N-(mercaptoalkyl)urea or carbamate/oral ANF, oral N-(mercaptoalkyl)urea or carbamate/parenteral ACE inhibitor, parenteral N-(mercaptoalkyl)urea or carbamate/oral ANF, parenteral N-(mercaptoalkyl)urea or carbamate/parenteral ACE inhibitor.

When the components of a combination of an N-(mercaptoalkyl)urea or carbamate and an ANF are administered separately, it is preferred that the N-(mercaptoalkyl)urea or carbamate be administered first.

The present invention also relates to a pharmaceutical composition comprising an N-(mercaptoalkyl)urea or carbamate for use in treating hypertension or congestive heart failure, to a pharmaceutical composition comprising both an N-(mercaptoalkyl)urea or carbamate and an ANF and to a pharmaceutical composition comprising both an N-(mercaptoalkyl)urea or carbamate and an ACE inhibitor.

The antihypertensive effect of N-(mercaptoalkyl)ureas or carbamates was determined according to the following procedure:

Male Sprague Dawley rats weighing 100–150 g were anesthetized with ether and the right kidney was removed. Three pellets containing DOC acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17–30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or N-(mercaptoalkyl)urea or carbamate and blood pressure was monitored for the next 4 hours.

A similar procedure can be used to determine the effect of N-(mercaptoalkyl)ureas or carbamates in combination with ACE inhibitors.

The antihypertensive effect of N-(mercaptoalkyl)ureas or carbamates in combination with ANF can be determined according to the following procedures:

Male spontaneously hypertensive rats (SHR), 16–18 weeks old, 270–350 g, are anesthetized with ether and the abdominal aorta is cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 ml/hr. Animals are allowed a 90-min equilibration period. The animals first undergo a challenge with an ANF such as atriopeptin II (AP il) or AP28 30 $\mu$g/kg iv and at the end of 60 min. are treated with drug vehicle or an N-(mercaptoalkyl)urea or carbamate subcutaneously. A second ANF challenge is administered 15 min. later and blood pressure is monitored for the next 90 min.

The antihypertensive effect in SHR of N-(mercaptoalkyl)urea or carbamates and ACE inhibitors, alone and in combination, can be determined as follows:

Animals are prepared for blood pressure measurement as described above. After stabilization, animals are dosed subcutaneously or orally with test drugs or placebo and blood pressure is monitored for the next 4 hr.

The compounds having structural formulae I and II have also been found to inhibit the activity of enzymes designated enkephalinases. The compounds are particularly useful for the inhibition of enkephalinase A, which is derived from the striata of both rats and humans. In in vitro tests, using test procedures for enkephalinase A inhibition well known to those skilled in the art, selected compounds having structural formula I and II have been found to inhibit the activity of the aforementioned enzyme. Therefore, the present invention also relates to a method for treating pain by inhibiting the action of enkephalinases in a mammal with a compound of formula I or II. and to analgesic pharmaceutical compositions comprising compounds of formula I or II.

The use of atrial natriuretic peptides in the treatment of nephrotoxicity associated with the immunosuppressive cyclosporin was reported by Capasso et al in the *American Journal of Hypertension.* 3, 3 (1990), p. 204–210. Since compounds of this invention enhance endogenous ANF, they can be used alone to treat nephrotoxicity, or they can be administered in combination with exogenous ANF.

The compositions of this invention comprise an N-(mercaptoalkyl)urea or carbamate, an N-(mercaptoalkyl)urea or carbamate and an ANF or an N-(mercaptoalkyl)urea or carbamate and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily dose of the compound or combinations of this invention for treatment of hypertension or congestive heart failure is as follows: for N-(mercaptoalkyl)ureas or carbamates alone the typical dosage is 0.1 to 10 mg/kg of mammalian weight per day administered in single or divided dosages; for the combination of an N-(mercaptoalkyl)urea or carbamate and an ANF, the typical dosage is 0.1 to 10 mg of N-(mercaptoalkyl)urea or carbamate/kg mammalian weight per day in single or divided dosages plus 0.001 to 0.1 mg ANF/kg of mammalian weight per day, in single or divided dosages, and for the combination of an N-(mercaptoalkyl)urea or carbamate and an ACE inhibitor, the typical dosage is 0.1 to 10 mg of N-(mercaptoalkyl)urea or carbamate/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension or congestive heart failure, the compounds or combinations of this invention may be administered to patients in a dosage range as follows: for treatment with an N-(mercaptoalkyl)urea or carbamate alone, about 5 to about 500 mg per dose given 1 to 4 times a day, giving a total daily dose of about 5 to 2000 mg per day; for the combination of an N-(mercaptoalkyl)urea or carbamate and ANF, about 5 to about 500 mg N-(mercaptoalkyl)urea or carbamate per dose given 1 to 4 times a day and about 0.01 to about 1 mg ANF given 1 to 6 times a day (total daily dosage range of 5 to 2000 mg day and 0.01 to 6 mg/day, respectively); and for the combination of an N-(mercaptoalkyl)urea or carbamate and an ACE inhibitor, about 5 to about 500 mg N-(mercaptoalkyl)urea or carbamate per dose given 1 to 4 times a day and about 5 to about 50 mg ACE inhibitor given 1 to 3 times a day (total daily dosage range of 5 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

To produce an analgesic effect, compounds of this invention will be administered in a dosage range of from about 1 to about 100 mg/kg. The doses are to be administered at intervals of from 3 to 8 hours. However, the quantity and frequency of dosage will depend upon such factors as the severity of the pain, the general physical condition of the patient, the age and weight of the patient, and other factors recognized by the skilled clinician.

For treatment of edema, renal insufficiency or nephrotoxicity associated with immunosuppressive therapy, dosage ranges of the compounds of this invention are the same as for treatment of hypertension with the use of N-(mercaptoalkyl)ureas or carbamates alone or in combination with ANF.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; nonionic, cationic and anionic surfactants; ethylene gylcol polymers; betacyclodextrin; fatty alcohols and hydrolyzed cereal solids; as well as other nontoxic compatible fillers, binders, disintegrants, buffers, preservatives, antioxidants, lubricants, flavoring agents, and the like commonly used in pharmaceutical formulations.

Since the present invention relates to treatment of hypertension or congestive heart failure with a combination of active ingredients wherein said active ingredients may be administered separately, the invention also relates to combining separate pharmaceutical compositions in kit form. That is, two kits are contemplated, each combining two separate units: an N-(mercaptoalkyl)urea or carbamate pharmaceutical composition and an ANF pharmaceutical composition in one kit and an N-(mercaptoalkyl)urea or carbamate pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are examples of procedures for preparing compounds of formulae I and II.

PREPARATION 1

1(R)-Acetylthio-3-(2-Methylphenyl)-2-Propylisocyanate

Heat for 1 hr at 80° C. a solution of 2(S)-acetylthiomethyl-3-(2-methylphenyl)-propionic acid (6.0 g=24 mmole), diphenylphosphoryl azide (6.6 g=24 mmole) and triethylamine (2.4 g=24 mmol) in toluene (90 ml). Allow to cool to obtain a clear solution containing the title isocyanate.

PREPARATION 2

1(R)-Acetylthio-3-(2-Methylphenyl)-2-Propylamine Hydrobromide

To the isocyanate solution of Preparation 1 (24 mmol), add benzyl alcohol (3.1 g=29 mmol) and heat at 80° C. for 1 hr. Concentrate in vacuo and partition with EtOAc and 1N NaHCO$_3$. Dry and concentrate to obtain crude benzyl N-[1(R)-acetylthio-3-(2-methylphenyl)-2-propyl]carbamate. Purify by silica gel chrornatography, eluting with hexane:Et$_2$O (2:1) to obtain a white solid, m.p. 73°-8° C., $[\alpha]_D^{26} = -2.0°$ (EtOH).

Add the resultant carbamate (3.2 g=9.0 mmol) to 33% HBr/HOAc (20 ml). After 4.5 hr, concentrate in vacuo. Treat the solid with Et$_2$O (200 ml), filter and dry to obtain the title compound as a pale orange solid, m.p. 137°-8° C.

EXAMPLE 1

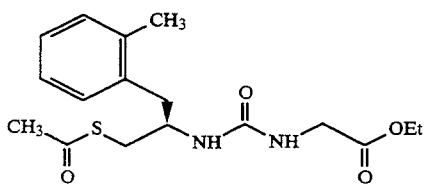

To the hydrobromide of Preparation 2 (0.45 g=1.5 mmol) and ethyl isocyanatoacetate (0.21 g=1.6 mmol) in CH$_2$Cl$_2$ (25 ml), add triethylamine (0.16 g=1.6 mmol). Stir 18 hr, concentrate in vacuo, and partition with EtOAc and 1N HCl. Dry and concentrate to obtain a gum. Chromatograph on silica gel, eluting with 20% hexane:Et$_2$O to obtain the title compound as a gum, $[\alpha]_D^{26} = -13.8°$ (EtOH).

EXAMPLE 2

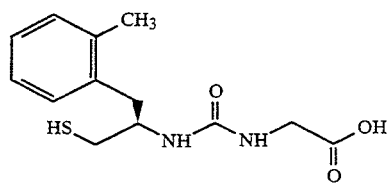

To the ester of Example 1 (0.21 g=0.59 mmol) in EtOH (10 ml, nitrogen-purged), add 1.0N NaOH (3.0ml, nitrogen-purged). Stir 0.5 hr, concentrate in vacuo, and add 1.0N HCl (3.0 ml). Extract with EtOAc, dry and concentrate to obtain the title compound as a gum, $[\alpha]_D^{26} = +13.3°$ (EtOH).

EXAMPLE 3

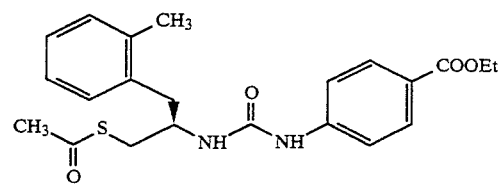

To the hydrobromide of Preparation 2 (0.45 g=1.5 mmol) and ethyl 4-isocyanatobenzoate (0.38 g=2.0 mmol) in CH$_2$Cl$_2$ (25 ml) add triethylamine (0.20 g=2.0 mmol). Stir 3 hr, concentrate in vacuo, and partition with EtOAc and 1N HCl. Dry and concentrate to obtain an oil. Chromatograph on silica gel, eluting with hexane:Et$_2$O (4:6) to obtain the title compound as a white solid, m.p. 84° C.

EXAMPLE 4

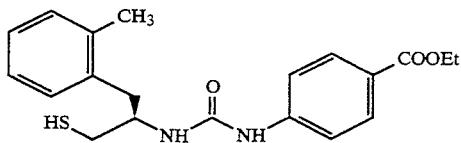

To the ester of Example 3 (0.23 g=0.55 mmol) in EtOH (8 ml, nitrogen-purged), add 1.00N NaOH (3.0ml, nitrogen-purged). Stir 1 hr, concentrate in vacuo and add 1.0N HCl (3.0 ml). Extract with EtOAc, dry and concentrate to obtain the title compound as a gum, $[\alpha]_D^{26} = +31.8°$ (EtOH).

EXAMPLE 5

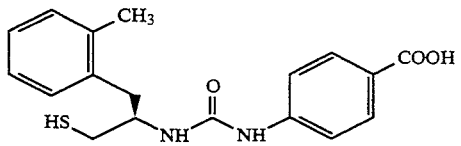

To the ester of Example 3 (0.23 g=0.55 mmol) in EtOH (8 ml, nitrogen-purged), add 1.00N NaOH (3.0 ml, nitrogen-purged). Stir 72 hr, concentrate in vacuo and add 1.0N HCl (3.0 ml). Filter the solid and chromatograph on silica gel, eluting with CH$_2$Cl$_2$:MeOH:-

HOAc (95:4:0.5) to obtain the title compound as a white solid, MS: M+1=326.

EXAMPLE 6

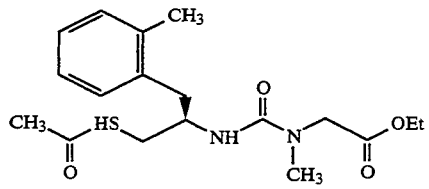

To the isocyanate solution of Preparation 1 (3.0 mmol), add sarcosine ethyl ester (liberated from the hydrochloride, 0.55 g=4.7 mmol). Heat at reflux 1 hr and concentrate in vacuo. Partition with EtOAc and 1N NaHCO₃, dry and concentrate. Chromatograph on silica gel, eluting with hexane:Et₂O (1:3) to obtain the title compound as an oil, $[\alpha]_D^{26}= -12.5°$ (EtOH).

EXAMPLE 7

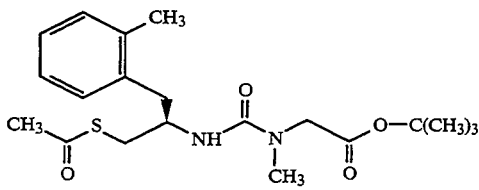

In a manner similar to Example 6, use sarcosine t-butyl ester to obtain the title compound, a gum, $[\alpha]_D^{26}= -16.1°$ (EtOH).

EXAMPLE 8

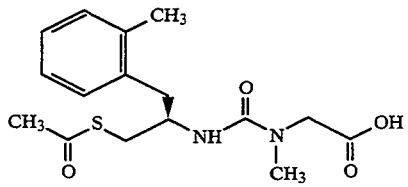

Dissolved the ester of Example 7 (0.49 g=1.24 mmol) in CF₃COOH (20 ml). After 0.5 hr, concentrate and partition between CH₂Cl₂—H₂O. Dry and concentrate to obtain the title compound, a solid, m.p. 119° C.

EXAMPLE 9

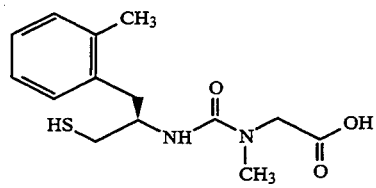

Dissolve the acid of Example 8 (0.21 g=0.62 mmol) in 1.0N NaOH (2.0 ml, nitrogen-purged). After 5 min, add 1.0N HCl (2.0 ml). Extract with EtOAc, dry and concentrate to obtain the title compound, a gum, $[\alpha]_D^{26}= +15.0°$ (EtOH).

EXAMPLE 10

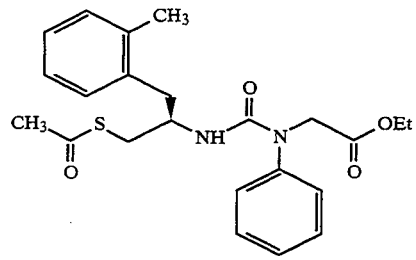

In a manner similar to Example 6, use N-phenylglycine ethyl ester to obtain the title compound, a gum, $[\alpha]_D^{26}= +2.2°$ (EtOH).

EXAMPLE 11

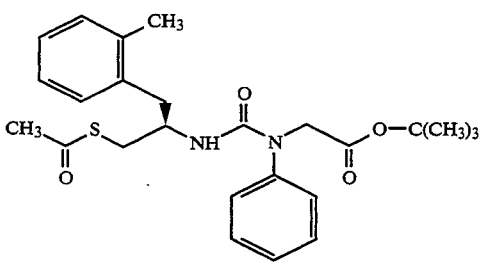

In a manner similar to Example 6, use N-phenylglycine t-butyl ester to obtain the title compound, a gum, $[\alpha]_D^{26}= +1.9°$ (EtOH).

EXAMPLE 12

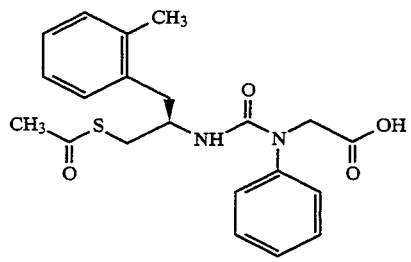

In similar fashion to Example 8, convert the ester of Example 11 to the title compound, a gum, $[\alpha]_D^{26}=0.0°$ (EtOH).

EXAMPLE 13

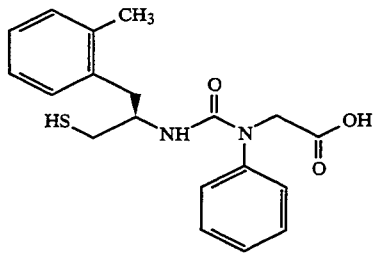

In a manner similar to Example 9, convert the acid of Example 12 to the title compound a solid, m.p. 143°–146°, $[\alpha]_D^{26}= +45.6°$ (EtOH).

EXAMPLE 14

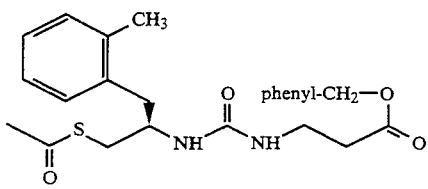

In a manner similar to Example 6, use β-alanine benzyl ester (liberated from the toluenesulfonate) to obtain the title compound, an oil, MS: M+1=429.

EXAMPLE 15

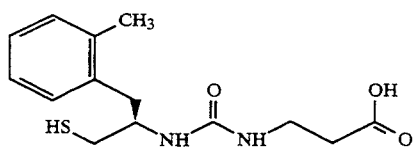

In a manner similar to Example 5 (1 hr reaction period), convert the ester of Example 14 to the title compound, a white solid, $[\alpha]_D^{26} = +11.4°$ (EtOH).

EXAMPLE 16

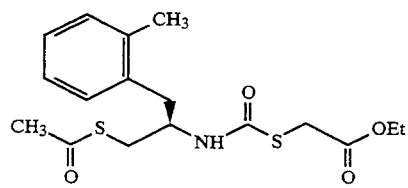

In a manner similar to Example 6, use ethyl mercaptoacetate to obtain the title compound, an oil, $[\alpha]_D^{26} = -35.0°$ (EtOH).

EXAMPLE 17

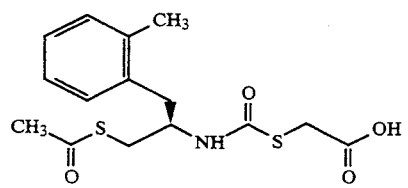

In a manner similar to Example 6, use mercaptoacetic acid to obtain the title compound, a foam, $[\alpha]_D^{26} = -32.0°$ (EtOH).

EXAMPLE 18

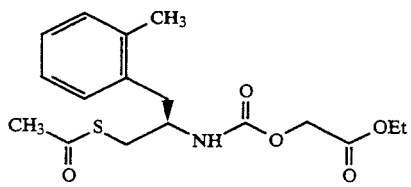

In a manner similar to Example 6, use ethyl glycolate to obtain the title compound, an oil, $[\alpha]_D^{26} = -28.8°$ (EtOH).

EXAMPLE 19

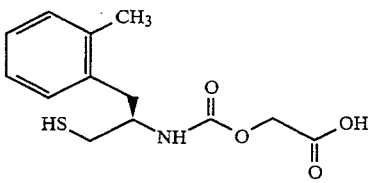

In a manner similar to Example 2, convert the ester of Example 18 to the title compound, a white solid, MS: M+1=284.

EXAMPLE 20

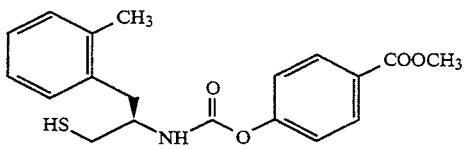

In a manner similar to Example 1, use 4-methoxycarbonylphenyl chloroformate, chromatographing on silica gel and eluting with 0.5% MeOH:CH₂Cl₂ to obtain the title compound as a pale yellow solid, m.p. 82°–83° C., $[\alpha]_D^{26} = -1.7°$ (EtOH).

EXAMPLE 21

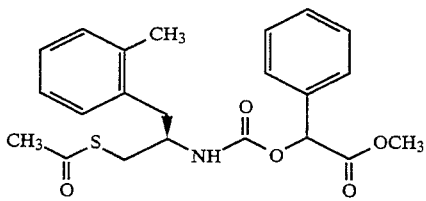

Add methyl (±)-mandelate (5.0 g=30 mmol) in toluene (50 ml) over 0.5 hr to 20% COCl₂/toluene (26.5 g=54 mmole COCl₂) at 0°. Add Et₃N (3.0 g=30 mmol) in toluene (10 ml) over 0.3 hr. Stir 3.5 hr, allow to warm, wash with H₂O, dry and concentrate to obtain the chloroformate as an oil. Use the resultant oil in the procedure of Example 1, chromatographing on silica gel and eluting with 1.5% MeOH/CH₂Cl₂ to obtain the title compound as an oil, $[\alpha]_D^{26} = -16.5°$ (EtOH).

EXAMPLE 22

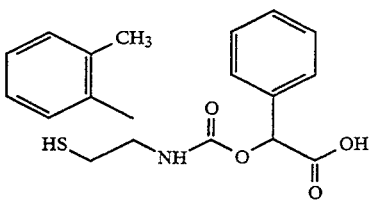

Treat the ester of Example 21 in a manner similar to Example 2, chromatographing on silica gel and eluting with CH₂Cl₂/MeOH/HOAc (95:4.5:0.5) to obtain the title compound as a solid, $[\alpha]_D^{26} = +21.5°$ (EtOH).

EXAMPLE 23

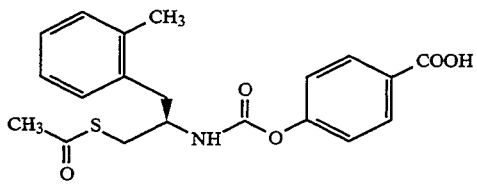

Combine t-butyl 4-hydroxybenzoate (0.75 g=3.9 mmol) with COCl₂ (20% toluene solution, 2.4 g=4.8 mmol), followed by N,N-dimethylaniline (0.46 g=3.9 mmol). Add CH₂Cl₂ (5 ml), stir 3 hr, and partition with EtOAc and 1.0N HCl. Concentrate, and treat the residue with more chloride and amine as above. Work up as before to obtain 4-(t-butoxycarbonyl)phenyl chloroformate as a gum. Employ this material in the procedure of Example 1 to obtain 4-(t-butoxycarbonyl)phenyl N-[1(R)-acetylthio-3-(2-methylphenyl)-2-propyl]carbamate, m.p. 95°–97° C. and 120° C.

In similar fashion to Example 8, convert the above ester to the title compound, a white solid, m.p. 189°–192° C., $[\alpha]_D^{26} = -1.9°$ (EtOH)-CH₂Cl₂).

Using the test procedures described above, compounds of examples 1 to 23 were found to produce a drop in blood pressure (ΔBP) in the DOCA salt model and in the ANF potentiation procedure:

| Example | RCO | Q | ANF[a] ΔBP (mmHg) | DOCA[b] ΔBP (mmHg) | dose mg/kg po |
|---|---|---|---|---|---|
| 1 | ⤳C(=O)-NH-CH₂-COOEt | Ac | 18 | 36 25 | 10 1 |
| 2 | ⤳C(=O)-NH-CH₂-COOH | H | 25 | 29 | 10 |
| 3 | ⤳C(=O)-NH-C₆H₄-COOEt | Ac | 13 | 10 | 10 |
| 4 | ⤳C(=O)-NH-C₆H₄-COOEt | H | 25 | 17 | 10 |
| 5 | ⤳C(=O)-NH-C₆H₄-COOH | H | — | 13 | 10 |
| 6 | ⤳C(=O)-N(CH₃)-CH₂-COOEt | Ac | 11 | 21 | 10 |
| 7 | ⤳C(=O)-N(CH₃)-CH₂-COOtBu | Ac | 12 | 9 | 10 |
| 8 | ⤳C(=O)-N(CH₃)-CH₂-COOH | Ac | 20 | — | — |

-continued

[Structure: 2-methylbenzyl group attached to chiral carbon bearing CH2-S-Q and NH-C(=O)-R]

| Example | RCO | Q | ANF$^a$ ΔBP (mmHg) | DOCA$^b$ ΔBP (mmHg) | dose mg/kg po |
|---------|-----|---|---------------------|----------------------|----------------|
| 9 | -C(=O)-N(CH3)-CH2-COOH | H | 25 | 9 | 10 |
| 10 | -C(=O)-N(Ph)-CH2-COOEt | Ac | 31 | 29 | 10 |
| 11 | -C(=O)-N(Ph)-CH2-COOtBu | Ac | — | 13 | 10 |
| 12 | -C(=O)-N(Ph)-CH2-COOH | Ac | 42 | 37 | 10 |
| 13 | -C(=O)-N(Ph)-CH2-COOH | H | 46 | 19 | 10 |
| 14 | -C(=O)-NH-CH2CH2-COOBn | Ac | — | 35 | 10 |
| 15 | -C(=O)-NH-CH2CH2-COOH | H | 47 | 10 | 10 |
| 16 | -C(=O)-S-CH2-COOEt | Ac | 14 | 24 | 10 |
| 17 | -C(=O)-S-CH2-COOH | Ac | 7 | 40 | 10 |
| 18 | -C(=O)-O-CH2-COOEt | Ac | 28 | 42 | 10 |

-continued

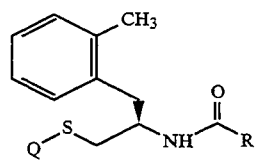

| Example | RCO | Q | ANF[a] ΔBP (mmHg) | DOCA[b] ΔBP (mmHg) | dose mg/kg po |
|---|---|---|---|---|---|
| 19 | ⱱO-C(=O)-O-CH2-COOH | H | 35 | 43 | 10 |
|  |  |  |  | 40 | 1 |
| 20 | ⱱO-C(=O)-O-C6H4-COOCH3 | Ac | 0 | 27 | 10 |
| 21 | ⱱO-C(=O)-O-CH(C6H5)-COOCH3 | Ac | 13 | 17 | 10 |
| 22 | ⱱO-C(=O)-O-CH(C6H5)-COOH | H | 15 | 26 | 10 |
| 23 | ⱱO-C(=O)-O-C6H4-COOH | Ac | — | 41 | 10 |
|  |  |  |  | 33 | 3 |

[a]Potentiation of ANF hypotensive response in SHR, increase relative to untreated controls [dose = 30 mg/kg (subcutaneous)]
[b]Antihypertensive response in DOCA rat, ΔMAP (po = oral)

The following formulations exemplify some of the dosage forms of the compositions of this invention. In each, the term "active ingredient" designates a compound of formula I or II, preferably $N^1$-[1(R)-acetylthio-3-(2-methylphenyl)-2-propyl]-$N^3$-(ethoxycarbonylmethyl)urea or carboxymethyl N-[1(R)-mercapto-3-(2-methylphenyl)-2-propyl]carbamate. However, these compounds can be replaced by equally effective amounts of other compounds of formula I or II.

EXAMPLE A

| | Tablets | | |
|---|---|---|---|
| No. | Ingredient | mg/tablet | mg/tablet |
| 1 | Active Compound | 100 | 500 |
| 2 | Lactose USP | 122 | 113 |
| 3 | Corn Starch, Food Grade, as a 10% Paste in Purified Water | 30 | 40 |
| 4 | Corn Starch, Food Grade | 45 | 40 |
| 5 | Magnesium Stearate | 3 | 7 |
|  | Total | 300 | 700 |

Method of Manufacture

Mix Items Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

| | Capsules | | |
|---|---|---|---|
| No. | Ingredient | mg/capsule | mg/capsule |
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|  | Total | 250 | 700 |

Method of Manufacture

Mix Item Nos 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

| Parenteral Preparation | | |
|---|---|---|
| Ingredient | mg/vial | mg/vial |
| Active Compound Sterile Powder | 100 | 500 |

For reconstitution add sterile water for injection or bacteriostatic water for injection.

We claim:
1. A compound having the structural formula

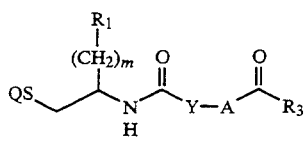

wherein:

A is a monocyclic or bicyclic arylene;

Q is hydrogen or $R_9CO-$;

Y is $-O-$, $-S-$ or $-NR_8-$;

$R_1$ is lower alkyl, cyclolower alkyl or aryl;

$R_8$ is hydrogen; lower alkyl; cyclolower alkyl; lower alkyl substituted with hydroxy, lower alkoxy, mercapto, lower alkylthio or aryl; or aryl;

$R_3$ is $-OR_5$ or $-NR_5R_6$;

$R_5$ and $R_6$ are independently selected from the group consisting of hydrogen, lower alkyl, hydroxy lower alkyl, lower alkoxy lower alkyl and aryl lower alkyl;

$R_9$ is hydrogen, lower alkyl or aryl; and m is 1 or 2;

or a pharmaceutically acceptable salt thereof.

2. A compound of claim 1 wherein $R_1$ is phenyl or lower alkyl substituted phenyl and m is 1.

3. A compound of claim 1 wherein $R_3$ is hydroxy or lower alkoxy.

4. A compound of claim 1 wherein Y is $-O-$, or $-NR_8-$ and $R_8$ is hydrogen, alkyl or phenyl.

5. A compound of claim 1 wherein A is phenylene.

6. A compound of claim 1 having the structural formula

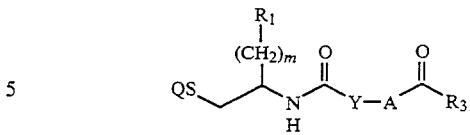

wherein m is 1, $R_1$ is 2-methylphenyl, A is 4-phenylene and wherein Q, Y and $R_3$ have the following values:

| Q | Y | $R_3$ |
|---|---|---|
| Ac | $-NH-$ | OEt |
| H | $-NH-$ | OEt |
| H | $-NH-$ | OH |
| Ac | $-O-$ | OMe |
| Ac | $-O-$ | OH | wherein Et is ethyl, Me is methyl and Ac is acetyl.

7. A method for treating hypertension, congestive heart failure, edema, renal insufficiency, nephrotoxicity or pain in mammals comprising administering to a mammal in need of such treatment: an effective amount of a compound of claim 1, alone or in combination with an atrial natriuretic factor or an angiotensin converting enzyme inhibitor.

8. A pharmaceutical composition for treating hypertension, congestive heart failure, edema, renal insufficiency, nephrotoxicity or pain in mammals comprising an effective amount of a compound of claim 1, alone or in combination with an atrial natriuretic factor or an angiotensin converting enzyme inhibitor, in a pharmaceutically acceptable carrier.

9. A composition of claim 8 wherein the atrial natriuretic peptide is chosen from α human AP 21, α human AP 28, α human AP 23, α human AP 24, α human AP 25, α human AP 26, α human AP 33, and the corresponding atrial peptides wherein the methionine at position 12 is replaced by isoleucine.

10. A composition of claim 8 wherein the angiotensin converting enzyme inhibitor is selected from: spirapril, enalapril, ramipril, perindopril, indolapril, lysinopril, quinapril, pentopril, cilazapril, captopril, zofenopril, pivalopril and fosinopril.

* * * * *